(12) United States Patent
Messer et al.

(10) Patent No.: US 6,602,891 B2
(45) Date of Patent: Aug. 5, 2003

(54) MUSCARINIC RECEPTOR AGONISTS

(75) Inventors: William S. Messer, Toledo, OH (US); Yang Cao, Toledo, OH (US)

(73) Assignee: The University of Toledo, Toledo, OH (US)

( * ) Notice: Subject to any disclaimer, the term of this patent is extended or adjusted under 35 U.S.C. 154(b) by 14 days.

(21) Appl. No.: 10/034,229

(22) Filed: Dec. 20, 2001

(65) Prior Publication Data

US 2003/0032658 A1 Feb. 13, 2003

Related U.S. Application Data

(62) Division of application No. 09/772,143, filed on Jan. 29, 2001, now Pat. No. 6,376,675, which is a continuation-in-part of application No. 09/629,029, filed on Jul. 31, 2000, now Pat. No. 6,369,081, which is a division of application No. 09/236,030, filed on Jan. 22, 1999, now Pat. No. 6,096,767.

(51) Int. Cl.$^7$ ............................................. A61K 31/433
(52) U.S. Cl. ..................................... 514/342; 546/268.1
(58) Field of Search ........................ 546/268.1; 514/342

(56) References Cited

U.S. PATENT DOCUMENTS

| | | | |
|---|---|---|---|
| 5,414,009 A | 5/1995 | Olesen et al. ................ | 514/299 |
| 5,712,297 A | 1/1998 | Sauerberg et al. | |
| 5,718,912 A | 2/1998 | Thomspon et al. .......... | 424/427 |
| 6,096,767 A | 8/2000 | Rajeswaran et al. ......... | 514/333 |

FOREIGN PATENT DOCUMENTS

| | | |
|---|---|---|
| EP | 0 384 288 A2 | 8/1990 |
| WO | WO93/14089 | 7/1993 |

OTHER PUBLICATIONS

Per Sauerberg, Preben H. Olesen, Susanne Nielsen, Svend Treppendahl, Malcolm J. Sheardown, Tage Honore, Charles H. Mitch, John S. Ward, Andrew J. Pike, Frank P. Bymaster, Berry D. Sawyer and Harlan E. Shannon, *Novel Functional $M_1$ Selective Muscarinic Agonists. Synthesis and Structure–Activity Relationships of 3–(1,2,5–Thiadiazolyl)–1,2,5, 6–tetrahydro–1–methylpyridines*, J. Med. Chem. (1992), 35, pp. 2274–2283.

Philip G. Dunbar, Graham J. Durant, Zheng Fang, Yahaya F. Abuh, Afif A. El–Assadi, Dan O. Ngur, Sumudra Periyasamy, Wayne P. Hoss and Williams S. Messer, Jr., *Design, Synthesis, and Neurochemical Evaluation of 5–(3–Alkyl–1, 2,4–oxadiazol–5–yl)–1,4,5,6–tetrahydropyrimidines as $M_1$ Muscarinic Receptor Agonists*, J. Med. Chem. (1993), 36, pp. 842–847.

John S. Ward, Leander Merritt, David O. Calligaro, Franklin P. Bymaster, Harlan E. Shannon, Charles H. Mitch, Celia Whitesitt, David Brunsting, Malcolm J. Sheardown, Preben H. Olesen, Michael D.B. Swedberg, Lone Jeppesen, and Per Sauerberg, *1,2,5–Thiadiazole Analogues of Aceclidine as Potent $m_1$ Muscarinic Agonists*, J. Med. Chem. (1998), 41, pp. 379–392.

Per Sauerberg, Lone Jeppesen, Preben H. Olesen, Thoger Rasmussen, Michael D.B. Swedberg, Malcolm J. Sheardown, Anders Fink–Jensen, Christian Thomsen, Henning Thogersen, Karin Rimvall, John S. Ward, David O. Calligaro, Neil W. DeLapp, Frank P. Bymaster and Harlan E. Shannon, *Muscarinic Agonists with Antipsychotic–like Activity: Structure–Activity Relationships of 1,2,5–Thiadiazole Analogues with Functional Dopamine Antagonist Activity*, J. Med. Chem. (1998), 41, pp. 4378–4384.

Lone Jeppesen, Preben H. Olesen, Lena Hansen, Malcolm J. Sheardown, Christian Thomsen, Thoger Rasmussen, Anders Fink Jensen, Michael S. Christensen, Karin Rimvall, John S. Ward, Celia Whitesitt, David O. Calligaro, Frank P. Bymaster, Neil W. DeLapp, Christian C. Felder, Harlan E. Shannon, and Per Sauerberg, *1,(1,2, 5–Thiadiazol–4–yl)–4–azatricyclo[2.2.1.0$^{2,6}$]heptanes as New Potent Muscarinic $M_1$ Agonists: Structure–Activity Relationship for 3–Aryl–2–propyn–1–yloxy and 3–Aryl–2–propyn–1–ylthio Derivatives*, J. Med. Chem. (1999), 42, pp. 1999–2006.

*Primary Examiner*—Jane Fan
(74) *Attorney, Agent, or Firm*—Emch, Schaffer, Schaub & Porcello Co. L.P.A.

(57) ABSTRACT

A compound of Formula (III):

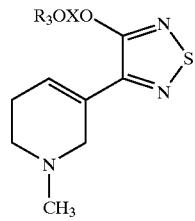

wherein X is a linkage independently selected from $(CH_2)_{12}$ or $(CH_2CH_2)_4O_3$ and wherein $R_3$ is independently selected from H, $CH_2CH_3$, $COCH_3$ or

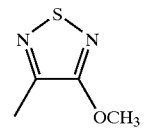

and acid addition salts, solvates and hydrates thereof. The compounds have unusually high affinity for muscarinic receptors, and exhibit agonist activity useful in the treatment of neurological and other disorders, in which stimulating cholinergic activity is desirable.

7 Claims, No Drawings

MUSCARINIC RECEPTOR AGONISTS

RELATED APPLICATIONS

The present invention is a division of Ser. No. 09/772,143, Jan. 29, 2001, now U.S. Pat. No. 6,376,675 which is a continuation-in-part of U.S. Ser. No. 09/629,029 filed Jul. 31, 2000, now U.S. Pat. No. 6,369,081 which is a divisional application of U.S. Ser. No. 09/236,030 filed Jan. 22, 1999, now U.S. Pat. No. 6,096,767 issued Aug. 1, 2000.

FIELD OF THE INVENTION

This invention relates to muscarinic receptor ligands with agonist activity. More particularly, this invention relates to compounds based on the tetrahydropyridyl moiety that have unusually high affinity for muscarinic receptors, and exhibit agonist activity useful in the treatment of neurological and other disorders, in which stimulating cholinergic activity is desirable.

BACKGROUND OF THE INVENTION

Recent advances have been made in the understanding of the cholinergic nervous system and the receptors therein. Cholinergic receptors are proteins embedded in the cell membrane that respond to the chemical acetylcholine. Cholinergic receptors are subdivided into the nicotinic and muscarinic receptor families, and muscarinic receptors represent a family of five subtypes.

Muscarinic receptors mediate a variety of physiological responses to the neurotransmitter acetylcholine in the central and peripheral nervous systems. $M_1$ muscarinic receptors play a role in learning and memory function in the brain and regulate gastric acid secretion in the stomach. $M_2$ receptors regulate acetylcholine release in the central nervous system and control cardiac muscle contraction. Acetylcholine stimulates smooth muscle contraction in a variety of tissues and promotes secretion from exocrine glands. These effects are mediated by $M_3$ receptors. Though less well characterized pharmacologically, $M_4$ receptors appear to play a role in the perception of pain, and $M_5$ receptors may regulate dopaminergic activity in the brain.

It has been suggested that compounds capable of mimicking the action of acetylcholine at these receptors would be useful in treating pathological conditions involving imbalances in these cholinergic pathways. Despite the wealth of knowledge about muscarinic receptor subtypes, relatively few selective ligands are available to characterize muscarinic receptor subtypes. Consequently, the tendency for ligands to bind indiscriminately to muscarinic receptor subtypes has made difficult the development of drugs that are muscarinic receptor subtype selective.

In view of the foregoing, it would be desirable to provide such compounds, particularly so side effects are minimized during treatment of the conditions noted above. It is an object of the present invention to provide compounds having muscarinic receptor affinity and activity. It is another object of the present invention to provide compounds having improved muscarinic receptor selectivity profiles. It is another object of the present invention to provide pharmaceutical composition comprising compounds of the present invention, as active ingredients.

SUMMARY OF THE INVENTION

According to one aspect of the present invention, there is provided a compound of Formula I:

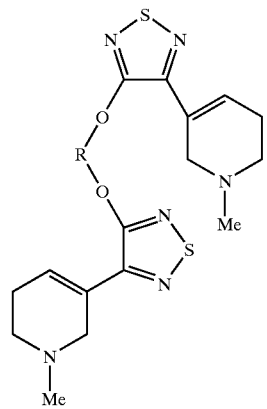

(I)

wherein R is a linkage independently selected from $(CH_2)_{12}$ or $(CH_2CH_2)_4O_3$, i.e., $CH_2CH_2OCH_2CH_2OCH_2CH_2OCH_2CH_2$—; and acid addition salts, solvates and hydrates thereof.

According to another aspect of the present invention, there is provided a compound of the Formula III:

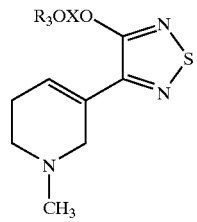

wherein X and R are
  IIIa=CDD-0297-A: X=$(CH_2)_{12}$, $R_1$=$R_2$=$R_3$=H
  IIIb=CDD-0299-A: X=$(CH_2)_{12}$, $R_1$=$R_2$=H, $R_3$=COCH$_3$
  IIIc=CDD-0300-A:
    X=$(CH_2CH_2OCH_2CH_2OCH_2CH_2OCH_2CH_2)$, $R_1$=$R_2$=$R_3$=H
  IIId=CDD-0301-A:
    X=$(CH_2CH_2OCH_2CH_2OCH_2CH_2OCH_2CH_2)$, $R_1$=$R_2$=$R_3$=CH$_2$CH$_3$
  IIIe=CDD-0303-A:
    X=$(CH_2CH_2OCH_2CH_2OCH_2CH_2OCH_2CH_2)$, $R_1$=$R_2$=H, $R_3$=COCH$_3$
  IIIf=CDD-0304-A:
    X=$(CH_2CH_2OCH_2CH_2OCH_2CH_2OCH_2CH_2)$, $R_1$=H, $R_2$=$R_3$=

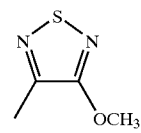

and acid addition salts, solvates and hydrates thereof.

According to another aspect of the present invention there is provided a pharmaceutical composition comprising compounds of Formula (I) or (III) and a pharmaceutically acceptable carrier.

DETAILED DESCRIPTION OF THE PREFERRED EMBODIMENTS

One aspect of the invention relates to bis-alkyloxy-1,2,5-thiadiazole derivatives of 1,2,5,6-tetrahydropyridine that bind to and activate muscarinic receptors. The compounds incorporate two functional muscarinic agonists into the same molecule with an alkyloxy linkage. More particularly, the present invention is directed to compounds of Formula (I):

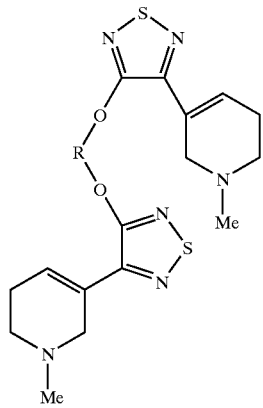

(I)

wherein R is a linkage independently selected from $(CH_2)_{12}$ or $(CH_2CH_2)_4O_3$, and acid addition salts, solvates and hydrates thereof.

According to another aspect of the present invention, there is provided a compound of the Formula III:

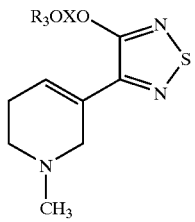

wherein X and R are

IIIa=CDD-0297-A: X=$(CH_2)_{12}$, $R_1$=$R_2$=$R_3$=H

IIIb=CDD-0299-A: X=$(CH_2)_{12}$, $R_1$=$R_2$=H, $R_3$=$COCH_3$

IIIc=CDD-0300-A: X=$(CH_2CH_2OCH_2CH_2OCH_2CH_2OCH_2CH_2)$, $R_1$=$R_2$=$R_3$=H

IIId=CDD-0301-A: X=$(CH_2CH_2OCH_2CH_2OCH_2CH_2OCH_2CH_2)$, $R_1$=$R_2$=$R_3$=$CH_2CH_3$

IIIe=CDD-0303-A: X=$(CH_2CH_2OCH_2CH_2OCH_2CH_2OCH_2CH_2)$, $R_1$=$R_2$=H, $R_3$=$COCH_3$

IIIf=CDD-0304-A: X=$(CH_2CH_2OCH_2CH_2OCH_2CH_2OCH_2CH_2)$, $R_1$=H, $R_2$=$R_3$=

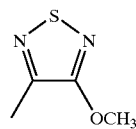

and acid addition salts, solvates and hydrates thereof.

The compounds of Formula (I), 2,2'-bis-{[3-(1-methyl-1,2,5,6-tetrahydropyrid-3-yl)-1,2,5-thiadiazol-4-yloxy]ethyloxy}-diethyl ether and 1,12-bis-[3-(1-methyl-1,2,5,6-tetrahydropyrid-3-yl)-1,2,5-thiadiazol-4-yloxy]-dodecane, exhibit very high affinity for muscarinic receptors as compared to the parent compound xanomeline. In addition, the compounds appear to interact with multiple $M_2$ receptors expressed in A9 L cells. It is believed that compounds of Formula (I) may act as agonists at muscarinic receptors coupled to the inhibition of adenylyl cyclase activity.

TABLE 1

| Ligand/ Linkage | M1 Receptors $K_1$ (nM) | % High affinity | M2 Receptors $K_h$ (pM) | $K_1$ (nM) |
|---|---|---|---|---|
| Xanomeline | 82 ± 6.7 | 26 ± 8.5 | 23 ± 16 | 32 ± 12 |
| $(CH_2)_6$ | 0.61 ± 0.18 | 18 ± 4.5 | 0.0086 ± 0.0069 | 0.28 ± 0.020 |
| $(CH_2)_8$ | 0.19 ± 0.040 | 40 ± 11 | 58 ± 56 | 0.38 ± 0.15 |
| $(CH_2)_{10}$ | 0.23 ± 0.10 | 26 ± 3.1 | 3.1 ± 2.4 | 0.23 ± 0.040 |
| $(CH_2CH_2)_4O_3$ | 0.12 ± 0.057 | — | — | — |

It was heretofore believed that as the length of the alkoxy chain increases agonist activity decreases. As reported in the Journal of Medicinal Chemistry, 1993, Vol. 36, No. 7, pages 843–844, increasing the length of the 3-alkyl chain on the 1,2,4-oxadiazole ring of 1,4,5,6-tetrahydropyrimidine dramatically decreased activity in the phosphoinositide metabolism assay. Again these data are consistent with similar observations in 1,2,4-oxadiazole derivatives of 1,2,5,6-tetrahydro-1-methylpyridine and quinuclidine where increasing the length of the 3-alkyl substituent led to compounds with higher affinity yet lower agonist activity. As shown in Tables 1 and 2, it has been surprisingly found that compounds of Formula I with increasing alkoxy chains displayed $M_1$ agonist efficacy comparable to xanomeline, yet with higher potency and higher affinity for $M_1$ receptors.

The receptor binding properties and agonist activity of bis-thiadiazole derivatives, (Formula (II)), at $M_1$ muscarinic receptors expressed in A9 L cells is provided below in Table 2. PI metabolism represents the percentage stimulation above basal levels at 100 μM expressed relative to the carbachol response (100%). Full dose-response curves were obtained for a few compounds. The data represents the mean (±s.e.m.) from two to five assays for each compound.

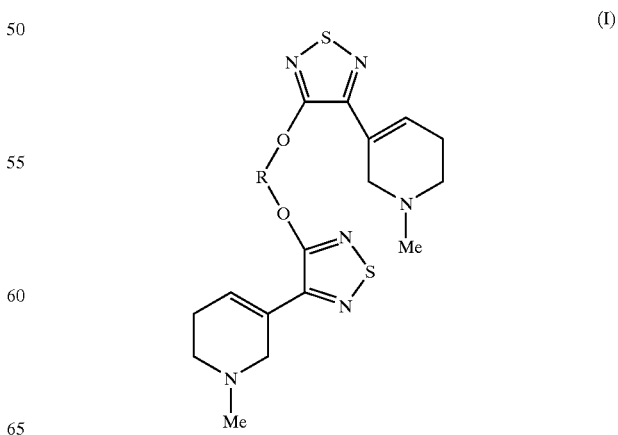

(I)

wherein R is a linkage independently selected from $(CH_2)_2$, $(CH_2)_3$, $(CH_2)_4$, $(CH_2)_5$, $(CH_2)_6$, $(CH_2)_7$, $(CH_2)_8$, $(CH_2)_9$, $(CH_2)_{10}$, $(CH_2)_{12}$ and $(CH_2CH_2)_4O_3$.

TABLE 2

| Compound/Linkage | PI metabolism | $EC_{50}$ ($\mu M$) | $S_{max}$ |
|---|---|---|---|
| Xanomeline | n.d. | 5.7 ± 2.3 | 180 ± 24% |
| $(CH_2)_2$ | 50 ± 14% | — | — |
| $(CH_2)_3$ | 21 ± 2.6% | — | — |
| $(CH_2)_4$ | 21 ± 1.9 | — | — |
| $(CH_2)_5$ | −1.0 ± 1.8% | — | — |
| $(CH_2)_6$ | 18 ± 0.06% | — | — |
| $(CH_2)_7$ | −3.0 ± 3.4% | — | — |
| $(CH_2)_8$ | 8.2 ± 1.4% | — | — |
| $(CH_2)_9$ | 27 ± 6.2% | 0.72 ± 0.37 | 140 ± 34% |
| $(CH_2)_{10}$ | 76 ± 11% | — | — |
| $(CH_2)_{12}$ | 84 ± 9.9 | 0.34 ± 0.19 | 190 ± 61% |
| $(CH_2CH_2)_4O_3$ | — | 0.0085 ± 0.0012 | 250 ± 36% |

The compounds of Formula III are based on the Formula I bivalent xanomeline derivatives described in the Example 1. The Formula I compounds exhibited high affinity and receptor activity, but their utility was limited by poor oral bioavailability and low CNS penetration, which is believed to be due to the large size and presence of two tertiary amines, which are both positively charged at physiological pH.

The compounds of Formula III incorporate hydrogen bonding elements as ester isosteres (i.e., alcohols, esters, 1,2,5-thiadiazoles) at the end of an alkyl or alkyloxy linking group as shown below. The compounds lack a second tetrahydropyridine moiety. Examples of the compounds of Formula III are shown in Table 3. The compounds of Formula III bind to $M_1$ muscarinic receptors and activate phosphoinositide metabolism in A9 L cells. The compounds of Formula III exhibit increased bioavailability and improved CNS penetration, as compared to the compounds of Formula I.

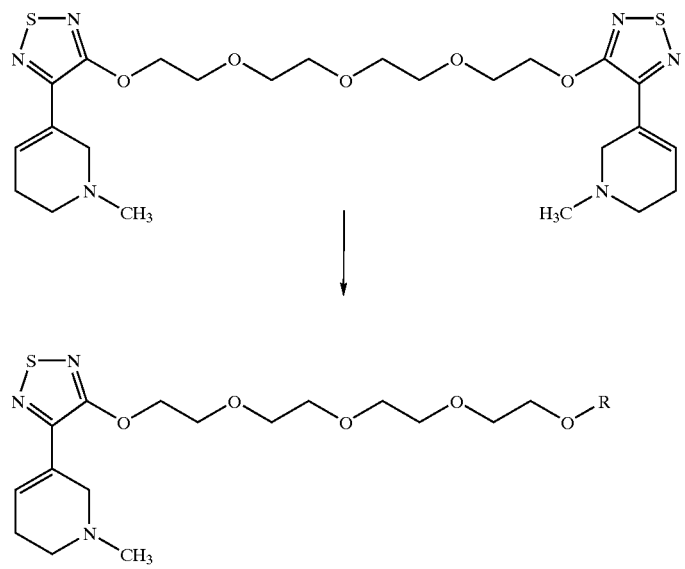

R = H, acetyl, ethyl, 4-methoxy-1,2,5-thiadiazol-3-yl

TABLE 3

Muscarinic Agonists

| Compound | Structure | Muscarinic receptor binding $K_i$ value | Phosphoinositide metabolism $S_{max}$ $EC_{50}$ |
|---|---|---|---|
| CDD-0297-A | 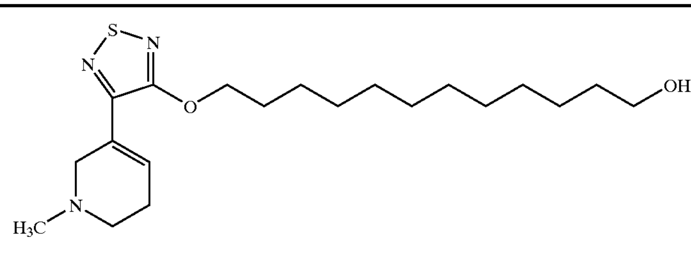 | 16 ± 3.1 nM | 250 ± 28% 2.6 ± 0.18 $\mu M$ |

TABLE 3-continued

Muscarinic Agonists

| Compound | Structure | Muscarinic receptor binding $K_i$ value | Phosphoinositide metabolism $S_{max}$ $EC_{50}$ |
|---|---|---|---|
| CDD-0299-A | 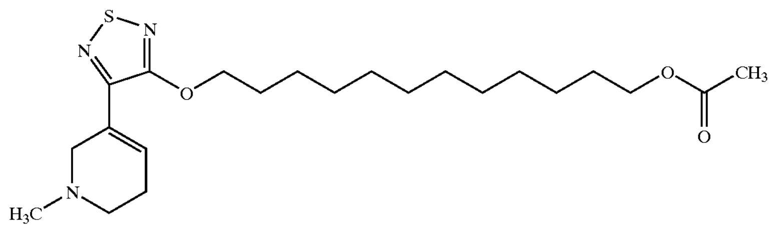 | 16 ± 13 nM | 280 ± 17% <br> 3.4 ± 1.6 μM |
| CDD-0300-A | 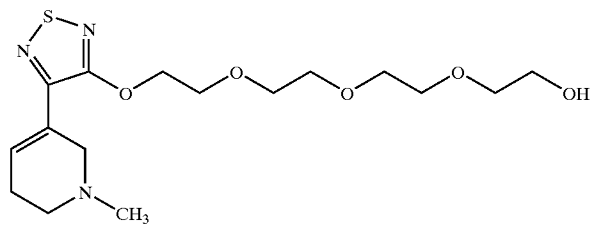 | 150 ± 42 nM | 240 ± 64% <br> 0.71 ± 0.17 μM |
| CDD-0301-A | 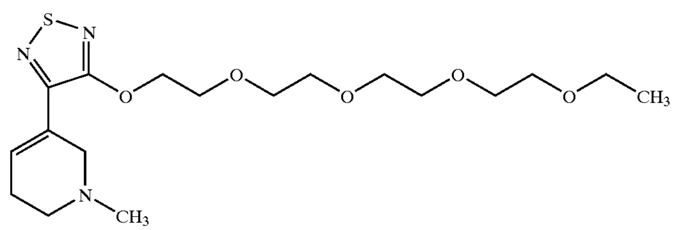 | 570 ± 220 nM | 420 ± 220% <br> 29 ± 23 μM |
| CDD-0303-A | 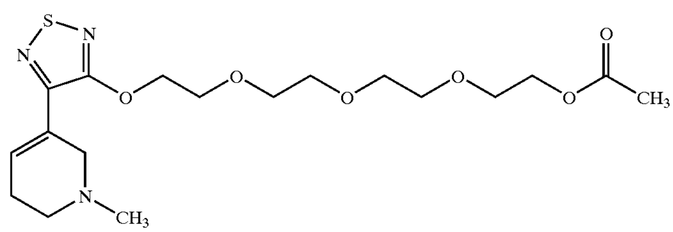 | 280 ± 130 nM | n.d. |
| CDD-0304-A | 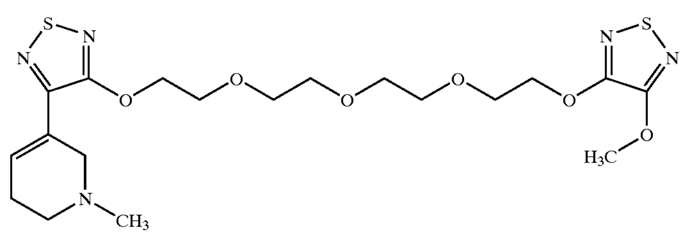 | 38 ± 23 nM | 600 ± 56% <br> 0.064 ± 0.016 μM |

The compounds of Formulae (I) and (III) are preferably isolated in substantially pure form.

The binding profiles of the compounds of Formulae (I) and (III) indicate their utility as pharmaceuticals useful for the treatment of various conditions in which the use of a muscarinic receptor ligand is indicated. More particularly, the compounds of Formulae (I) and (III) have been found to mimic acetylcholine function via an action at muscarinic receptors and are therefore of potential use in the treatment of pain, Alzheimer's disease and other disorders involving cholinergic deficits. Furthermore, it has been found that the inclusion of heteroatoms in the alkyl chain improves the water solubility of the compounds. In addition, agonist activity is enhanced relative to the straight chain derivatives.

The present invention also provides pharmaceutical compositions, which comprise compounds of Formulae (I) and (III) or pharmaceutically acceptable salts thereof, and pharmaceutically acceptable carriers. The pharmaceutical composition may be in the form of patches, tablets, capsules, powders, granules, lozenges, suppositories, reconsititutable powders or liquid preparations such as oral or sterile parenteral solutions or suspensions. The pharmaceutical composition includes compounds of Formulae (I) and (III) of a pharmaceutically acceptable level of purity excluding normal pharmaceutical additives such as diluents and carriers, and including no material considered toxic at normal dosage levels. A pharmaceutically acceptable level of purity will generally be at least 90% excluding normal pharmaceutical additives, preferably 95%; more preferably 97% and still more preferably 99%.

Sauerbeg et al., Journal Medicinal Chemistry, 1992, Vol. 35, page 2274, reported the synthesis and SAR of potent ligands of $M_1$ receptors based on the 1,2,5-thiadiazolyl-tetrahydropyridine moieties. In accordance with the present invention, is was found that if two 1,2,5-thiadiazolyl-tetrahydropyridine moieties are tethered by spacers of varied length and rigidity, in a single structure, the binding affinity of the resultant bis ligands is enhanced. By varying the length of the alkyl chain and also replacing some of the carbons with heteroatoms such as N, O or S, structure activity relationships is established. The two moieties in the same molecule may either bind in the pockets of two proximal receptors or in two pockets of the same receptor molecule.

The compounds of Formulae (I) and (III) can be prepared as described below.

The following is a detailed example of a preferred process to prepare compounds of Formulae (I) and (III). It will be understood that the following examples are not intended to limit the scope of the invention.

EXAMPLE 1

3-(3-chloro-1,2,5-thiadiazol-4-yl-pyridine (compound 1) was synthesized from 3-pyridinecarboxaldehyde following, except with slight modification, from the published procedure as provided in Sauerberg et al, Journal Medicinal Chemistry, 1992, Vol. 35, Page 2274. 3-(3-Chloro-1,2,5-thiadiazol-4-yl)pyridine was reacted with a diol (compound 2, wherein n=6, 7, 8, 9, 10 or 12) in the presence of sodium hydride in refluxing THF to yield bis[3-(pyridin-3-yl)-1,2, 5-thiadiazol-4-yl]alkyl-diethers (compound 3, wherein n=6, 7, 8, 9, 19 or 12) in 75–90% yield. These diethers were treated with excess methyl iodide in acetone or chloroform to give bis-quaternary ammonium iodides (compound 4, wherein n=6, 7, 8, 9, 10 or 12) in 96–100% yield. The quaternary salts were then treated with 5 equivalents of sodium borohydride in a mixture of methanol and chloroform to yield the compounds 5, wherein n=6, 7, 8, 9, 10 or 12 in 50–60% yield. Dry hydrogen chloride gas was then bubbled through the methanolic solution of compounds 5 at 0° C. to give compounds 6, wherein n=6, 7, 8, 9, 10 or 12 in 95–100% yield.

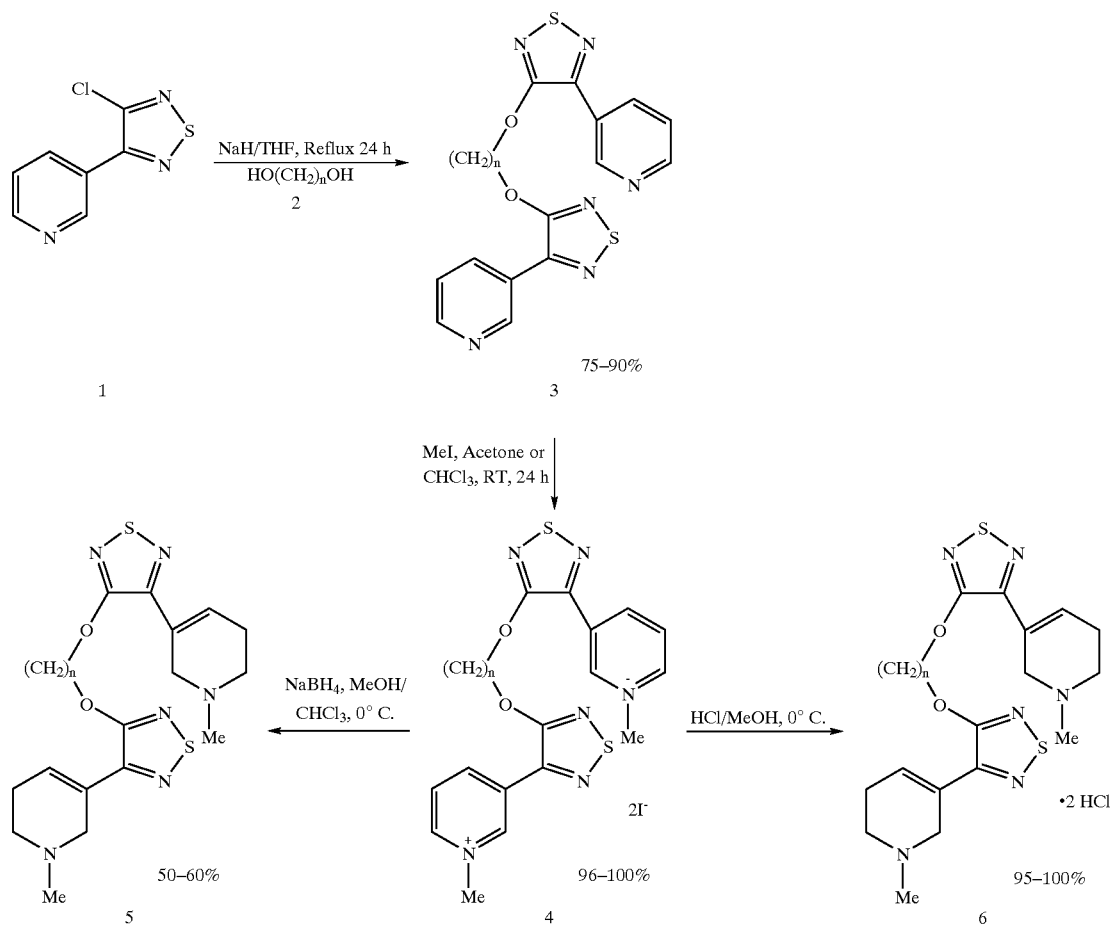

In view of the detailed description provided herein, it will be appreciated by one skilled in the art that the above bis-ligand methodology can include, but not be limited to, other known and potential muscarinic ligands such as tetrahydropyrimidine-oxadiazoles, tetrahydropyrimidine-thiadiazoles, quinuclidine-thiadiazoles, and the like.

(For CDD-0304-A, prior to quaternization, the resulting tetra(ethylene glycol)mono-[3-(pyrid-3-yl)-1,2,5-thiadiazol-4-yl]ether was reacted further with 3-chloro-4-methoxy-1,2,5-thiadiazole to give compound 3 where $R_1$ changed to 4-methoxy-1,2,5-thiadiazol-3-yl).

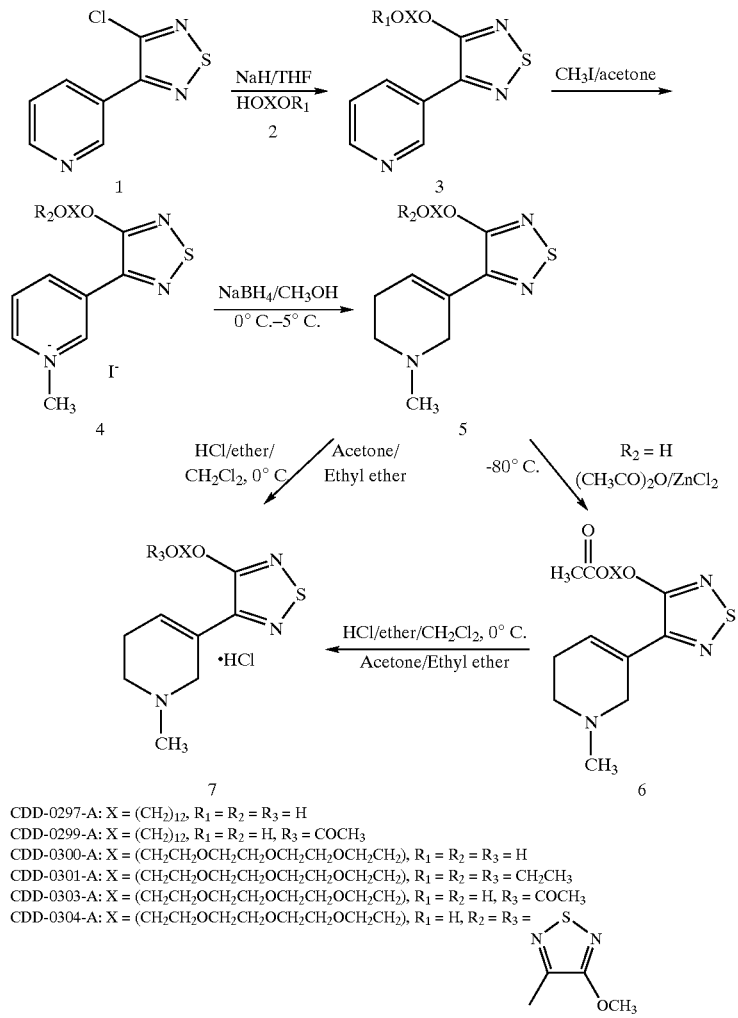

CDD-0297-A: X = $(CH_2)_{12}$, $R_1 = R_2 = R_3 = H$
CDD-0299-A: X = $(CH_2)_{12}$, $R_1 = R_2 = H$, $R_3 = COCH_3$
CDD-0300-A: X = $(CH_2CH_2OCH_2CH_2OCH_2CH_2OCH_2CH_2)$, $R_1 = R_2 = R_3 = H$
CDD-0301-A: X = $(CH_2CH_2OCH_2CH_2OCH_2CH_2OCH_2CH_2)$, $R_1 = R_2 = R_3 = CH_2CH_3$
CDD-0303-A: X = $(CH_2CH_2OCH_2CH_2OCH_2CH_2OCH_2CH_2)$, $R_1 = R_2 = H$, $R_3 = COCH_3$
CDD-0304-A: X = $(CH_2CH_2OCH_2CH_2OCH_2CH_2OCH_2CH_2)$, $R_1 = H$, $R_2 = R_3 =$

EXAMPLE 2

Preparation of mono-[3-(1-methyl-1,2,5,6-tetrahydropyrid-3-yl)-1,2,5-thiadiazol-4-yl]ether derivatives.

3-(3-Chloro-1,2,5-thiadiazol-4-yl)pyridine (compound 1) was synthesized from 3-pyridinecarboxlaldehyde following published procedures as provided in Sauerberg et al., Journal of Medicinal Chemistry, 1992, Vol. 35, page 2274. Tetra (ethylene glycol)mono ethyl ether was prepared from the reaction of tetra(ethylene glycol) with NaH and $BrCH_2CH_3$ in THF. 3-Chloro-4-methoxy-1,2,5-thiadiazole was synthesized by reacting 3,4-dichloro-1,2,5-thiadiazole with $NaOCH_3$.

3-(3-Chloro-1,2,5-thiadiazol-4-yl)pyridine was combined with compound 2 (1,12-dodecanediol, tetra(ethylene glycol), or tetra(ethylene glycol)mono ethyl ether) in the presence of NaH in refluxing THF to give mono-[3-(pyrid-3-yl)-1,2,5-thiadiazol-4-yl]ethers (compounds 3) in 40–60% yield.

The ethers were treated with excess $CH_3I$ in acetone to yield the quaternary ammonium iodides (compounds 4) in 85–90% yield.

The quaternary salts then were treated with 4 equivalents of $NaBH_4$ in $CH_3OH$ to yield the free bases (compounds 5) in 30–50% yield.

(For CDD-0299-A and CDD-0303-A, the free bases were converted into the corresponding acetyl esters (compounds 6) by reacting with excess acetic anhydride in the presence of catalytic anhydrous $ZnCl_2$ before conversion into hydrochlorides).

Ethereal HCl then was added into the methylene chloride solution of compounds 5 or 6, after crystallization from acetone/ether, and the final compounds 7 were obtained in 60–80% yield.

CDD-0297-A:
Formula IIIa
12-[3-(1-Methyl-1,2,5,6-tetrahydropyrid-3-yl)-1,2,5-thiadiazol-4-yloxy]-1-dodecanolhydrochloride, white powder, m.p. 97–98° C.;

CDD-0299-A:

Formula IIIb

12-[3-(1-Methyl-1,2,5,6-tetrahydropyrid-3-yl)-1,2,5-thiadiazol-4-yloxy]-1-dodecyl acetate hydrochloride, hygroscopic pale yellow powder, m.p. 85–86° C.;

CDD-0300-A:

Formula IIIc

Tetra(ethylene glycol)mono[3-(1-methyl-1,2,5,6-tetrahydropyrid-3-yl)-1,2,5-thiadiazol-4-yl]ether hydrochloride, yellow oil;

CDD-0301-A:

Formula IIId

Tetra(ethylene glycol)ethyl [3-1-methyl-1,2,5,6-tetrahydropyrid-3-yl)-1,2,5-thiadiazol-4-yl]ether hydrochloride, pale white powder, m.p. 64.5–66° C.;

CDD-0303-A:

Formula IIIe

Tetra(ethylene glycol)[3-(1-methyl-1,2,5,6-tetrahydropyrid-3-yl)-1,2,5-thiadiazol-4-yl]ether acetate hydrochloride, hygroscopic white-yellow powder, m.p. 55–55.5° C.;

CDD-0304-A:

Formula IIIf

Tetra(ethyleneglycol)(4-methoxy-1,2,5-thiadiazol-3-yl)[3-(1-methyl-1,2,5,6-tetrahydropyrid-3-yl)-1,2,5-thiadiazol-4-yl]ether hydrochloride, hygroscopic white-yellow powder, m.p. 35–37° C.

The patents, documents and publications described herein are hereby incorporated by reference.

Having described presently preferred embodiments of the invention, it is to be understood that it may be otherwise embodied within the scope of the appended claims.

We claim:

1. A method of treating a condition selected from pain and Alzheimer's disease comprising administering to a patient in need of such treatment a muscarinic agonistic effective amount of a compound of formula (III):

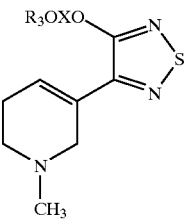

wherein X is a linkage independently selected from $(CH_2)_{12}$ or $(CH_2CH_2)_4O_3$; and wherein $R_3$ is independently selected from H, $CH_2CH_3$, $COCH_3$ or

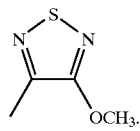

2. The method of claim 1, wherein the compound is 12-[3-(1-methyl-1,2,5,6-tetrahydropyrid-3-yl)-1,2,5-thiadiazol-4-yloxy]-1-dodecanol hydrochloride.

3. The method of claim 1, wherein the compound is 12-[3-(1-methyl-1,2,5,6-tetrahydropyrid-3-yl)-1,2,5-thiadiazol-4-yloxy]-1-dodecyl acetate hydrochloride.

4. The method of claim 1, wherein the compound is tetra(ethylene glycol)mono[3-(1-methyl-1,2,5,6-tetrahydropyrid-3-yl)-1,2,5-thiadiazol-4-yl]ether hydrochloride.

5. The method of claim 1, wherein the compound is tetra(ethylene glycol)ethyl[3-1-methyl-1,2,5,6-tetrahydropyrid-3-yl)-1,2,5-thiadiazol-4-yl]ether hydrochloride.

6. The method of claim 1, wherein the compound is tetra(ethylene glycol)[3-(1-methyl-1,2,5,6-tetrahydropyrid-3-yl)-1,2,5-thiadiazol-4-yl]ether acetate hydrochloride.

7. The method of claim 1, wherein the compound is tetra(ethylene glycol)(4-methoxy-1,2,5-thiadiazol-3-yl)[3-(1-methyl-1,2,5,6-tetrahydropyrid-3-yl)-1,2,5-thiadiazol-4-yl]ether hydrochloride.

* * * * *

UNITED STATES PATENT AND TRADEMARK OFFICE
CERTIFICATE OF CORRECTION

PATENT NO.     : 6,602,891 B2  
DATED          : August 5, 2003  
INVENTOR(S)    : William S. Messer and Yang Cao It is certified that error appears in the above-identified patent and that said Letters Patent is hereby corrected as shown below:

Column 14,
Line 20, please add -- or an acid addition salt, solvate or hydrate thereof --.

Signed and Sealed this

Twenty-fifth Day of November, 2003

JAMES E. ROGAN
*Director of the United States Patent and Trademark Office*